US012678317B2

(12) United States Patent (10) Patent No.: US 12,678,317 B2
Hsu et al. (45) Date of Patent: Jul. 14, 2026

(54) IMPACT GUARD FOR KNEE BRACE

(71) Applicant: OSSUR ICELAND EHF, Reykjavik (IS)

(72) Inventors: Henry Hsu, Foothill Ranch, CA (US); Tim Mcmorrow, Foothill Ranch, CA (US)

(73) Assignee: OSSUR ICELAND EHF, Reykjavik (IS)

( * ) Notice: Subject to any disclaimer, the term of this patent is extended or adjusted under 35 U.S.C. 154(b) by 0 days.

(21) Appl. No.: 18/848,570

(22) PCT Filed: Mar. 29, 2023

(86) PCT No.: PCT/US2023/016725
§ 371 (c)(1),
(2) Date: Sep. 19, 2024

(87) PCT Pub. No.: WO2023/192379
PCT Pub. Date: Oct. 5, 2023

(65) Prior Publication Data
US 2025/0228689 A1 Jul. 17, 2025

Related U.S. Application Data

(60) Provisional application No. 63/326,151, filed on Mar. 31, 2022.

(51) Int. Cl.
| | |
|---|---|
| *A61F 5/01* | (2006.01) |
| *A61F 7/00* | (2006.01) |
| *A63B 71/12* | (2006.01) |

(52) U.S. Cl.
CPC .............. *A61F 5/0123* (2013.01); *A61F 7/00* (2013.01); *A63B 71/1225* (2013.01);
(Continued)

(58) Field of Classification Search
CPC .......... A61F 5/0123; A61F 5/013; A61F 5/01; A61F 5/0118; A61F 5/0125;
(Continued)

(56) References Cited

U.S. PATENT DOCUMENTS

| | | | |
|---|---|---|---|
| 4,599,748 A | 7/1986 | Garcia | |
| 7,329,230 B2 * | 2/2008 | Mazzarolo | ............. A63B 71/12 |
| | | | 2/455 |

(Continued)

FOREIGN PATENT DOCUMENTS

| | | | |
|---|---|---|---|
| CN | 219396357 U | * | 7/2023 |
| EP | 2540259 A1 | | 1/2013 |
| WO | 2020038987 A1 | | 2/2020 |

OTHER PUBLICATIONS

Translation of CN 219396357 U provided by PE2E Search (Year: 2023).*

(Continued)

*Primary Examiner* — Daniel A Miller
(74) *Attorney, Agent, or Firm* — Workman Nydegger

(57) ABSTRACT

An impact guard for use with a knee brace includes a second shell secured to a padded liner, and a first shell disposed of over at least a portion of the second shell. The second shell is tethered to the first shell by an elastic cord, such that a second portion of the first shell slides over the first shell.

14 Claims, 9 Drawing Sheets

(52) U.S. Cl.
CPC .................. *A61F 2005/0181* (2013.01); *A61F 2005/0197* (2013.01); *A61F 2007/0042* (2013.01); *A61F 2007/0064* (2013.01); *A63B 2071/125* (2013.01)

(58) Field of Classification Search
CPC ...... A61F 5/3715; A61F 5/3723; A61F 5/373; A61F 5/3738; A61F 5/3753; A61F 5/37; A61F 5/3746; A61F 5/3761; A61F 5/02; A61F 5/0104; A61F 5/04; A61F 5/05; A61F 5/0585; A61F 5/05858; A61F 5/05866; A61F 5/058; A61F 7/00; A61F 2007/0042; A61F 2007/0064; A63B 71/08–148; A63B 2071/125; A63B 21/02; A63B 21/022; A63B 21/04; A63B 21/0407; A41D 13/065; A41D 13/0015; A41D 13/015; A41D 13/0153; A41D 13/0156; A41D 13/0158; A41D 13/05; A41D 13/06

USPC ........................................................ 602/14
See application file for complete search history.

(56) References Cited

U.S. PATENT DOCUMENTS

| | | | | |
|---|---|---|---|---|
| 10,420,668 | B2 | 9/2019 | Klutts | |
| 10,709,179 | B2 * | 7/2020 | Behrend | ............ A41D 13/0153 |
| 2003/0144620 | A1 * | 7/2003 | Sieller | .................. A61F 5/0125 |
| | | | | 602/5 |
| 2008/0195015 | A1 | 8/2008 | Ingimundarson et al. | |
| 2018/0153233 | A1 | 6/2018 | Paquette | |
| 2020/0306070 | A1 | 10/2020 | Hsu et al. | |
| 2021/0195969 | A1 * | 7/2021 | Mazzarolo | ............ A61F 5/0125 |

OTHER PUBLICATIONS

International Search Report from corresponding PCT Application No. PCT/US2023/016725, Jun. 27, 2023.

* cited by examiner

IMPACT GUARD FOR KNEE BRACE

FIELD OF THE DISCLOSURE

This disclosure relates to orthopedic braces, particularly a patella shell or impact guard for protecting the patella (kneecap) of a user's knee for use with a knee brace.

BACKGROUND

Orthopedic braces comprise a broad range of structures and devices used for supporting or stabilizing a joint when worn on a user's body. Orthopedic braces may serve in either preventative or remedial roles. In the preventative role, the brace can provide additional support, stability, and protection to a healthy joint to prevent or minimize injury due to undue stress. In the remedial role, the brace can support and strengthen a weakened joint due to injury or infirmity and reinforce the joint to prevent further injury or correct or assist in minimizing the effects of the infirmity.

Typically, orthopedic braces include a frame that comprises at least one support member. The brace may include rotational hinges that assist and control the limb's movement when there are multiple support members. In addition, suitable straps may maintain the brace on the limb, and other features, such as pads, may relieve the pressure of the brace on the limb and surrounding areas.

A predominant orthopedic brace is a knee brace. Knee braces stabilize the knee by preventing excessive knee movement or facilitating the controlled movement of the knee. Many braces comprise a frame having hinges on at least one of the lateral or medial sides of the knee joint. Straps are used to secure the brace to the leg or knee. An injured knee can be fit with an "off-the-shelf" brace or a "custom-fit" brace, depending on the size and shape of an individual's leg.

Many knee braces are arranged to reduce knee instability following an injury, or fatigue or to treat the impairment of the knee, particularly if the knee has damaged ligaments. Braces may be recommended for walking, skiing, running, motocross, or other activities involving twisting, pivoting, or jumping. Besides providing increased stability to the knee, braces may also decrease the risk of injuring the knee or leg or provide corrective assistance to the knee. One way of protecting the knee is by including attachments such as an impact guard, which may be secured onto the brace and configured to cover and protect the patella from impact during physical activities.

While knee braces including a protective patella shell or impact guard are available, those that are available are often complex, relatively expensive, and exhibit problems with fit and comfort, particularly to accommodate twisting, pivoting, and jumping activities such as are common in some physical sports, such as motocross and skiing. Because of these drawbacks, many knee braces and associated patella shells detract from the user's endeavor.

It is desired to provide a patella shell or impact guard for use with a knee brace that is relatively simple in construction, and yet may be easily secured to the knee brace, over the user's patella. It is likewise desired to allow the impact guard to accommodate movements associated with twisting, jumping, pivoting, etc., to maintain the impact guard in the desired position relative to the knee brace and the user's knee as a user participates in a physical activity such as motocross, skiing, or other physical sporting activities involving similar movements.

SUMMARY

According to embodiments of the disclosure, a patella shell or impact guard for use with a knee brace is provided to shield a patella from debris common to sports like motocross and mountain biking. The impact guard may include a lined second shell, and a first shell disposed over at least a portion of the second shell. The first and second shells may include venting features and may be lined with padding. The first and second shells are preferably rigid and impact resistant. The first and second shells define features enabling securement to a knee brace, such that the second shell may maintain a constant or fixed position and the first shell sliding or articulates over a portion of the second shell to permit simultaneous articulation of the knee brace, and hence a user's knee.

Details of the embodiments and variations thereof are provided in the following discussion in conjunction with the drawings.

Glossary

As used, the term "proximal" has its ordinary meaning and refers to a location next to or near the point of attachment or origin or a central point, or located toward the center of the body. Likewise, the term "distal" has its ordinary meaning and refers to a location situated away from the point of attachment or origin or a central point, or located away from the center of the body. The term "posterior" also has its ordinary meaning and refers to a location behind or to the rear of another location. Last, the term "anterior" has its ordinary meaning and refers to a location ahead of or to the front of another location.

The terms "rigid," "flexible," "compliant," and "resilient" may distinguish characteristics of material properties. The term "rigid" should denote that an devoid of flexibility. Within the context of features that are "rigid," it should indicate that they do not lose their overall shape when force is applied and may break if bent with sufficient force. The term "flexible" should denote that features are capable of repeated bending such that the features may be bent into retained shapes or the features retain no general shape, but continuously deform when force is applied.

Additional terms set forth below will have the meanings as defined:

"front" connotes an outward surface intended to be directed away from a knee of a wearer of the impact guard and is generally exposed to environmental conditions and protects the knee;

"rear" connotes an inward surface intended to face a knee of a wearer of the impact guard, and generally placed adjacent to the knee of the wearer and providing cushioning to the knee;

"shell" refers to a rigid or semi-rigid protective component adapted to cover at least a portion of a user's knee, and cooperating shells constitute a protective component for a user's knee;

"extended" means the position when the user's leg is straight;

"vent" means a cutout portion to encourage airflow;

"liner" means an internal portion of the impact guard added for additional comfort or padding, made of a different material than the shells;

"anchor point" means a portion of the impact guard that extends to attach to the frame of an orthopedic brace;

"post" means a thin portion of the impact guard that may be used to secure elements, add stability, or otherwise prevent movement;

"top" refers to the direction of the proximal end of the impact guard;

"bottom" refers to the direction of the distal end of the impact guard;

"EVA" stands for ethylene-vinyl acetate;

"ridge" means an area next to a depressed portion of the shell; this can run along the length of the shell; and "cooling channel" means an indented portion in the padding or design to encourage airflow, differing from a vent because it does not cut entirely through the shells.

BRIEF DESCRIPTION OF THE DRAWINGS

The drawing figures are not necessarily drawn to scale, but instead are drawn to provide a better understanding of the components thereof, and are not intended to be limiting in scope, but to provide exemplary illustrations. The figures illustrate exemplary configurations of an orthopedic device, and in no way limit the structures or configurations of a simplified polycentric hinge according to the present disclosure.

DETAILED DESCRIPTION OF VARIOUS EMBODIMENTS

A. Overview

Figure 1:
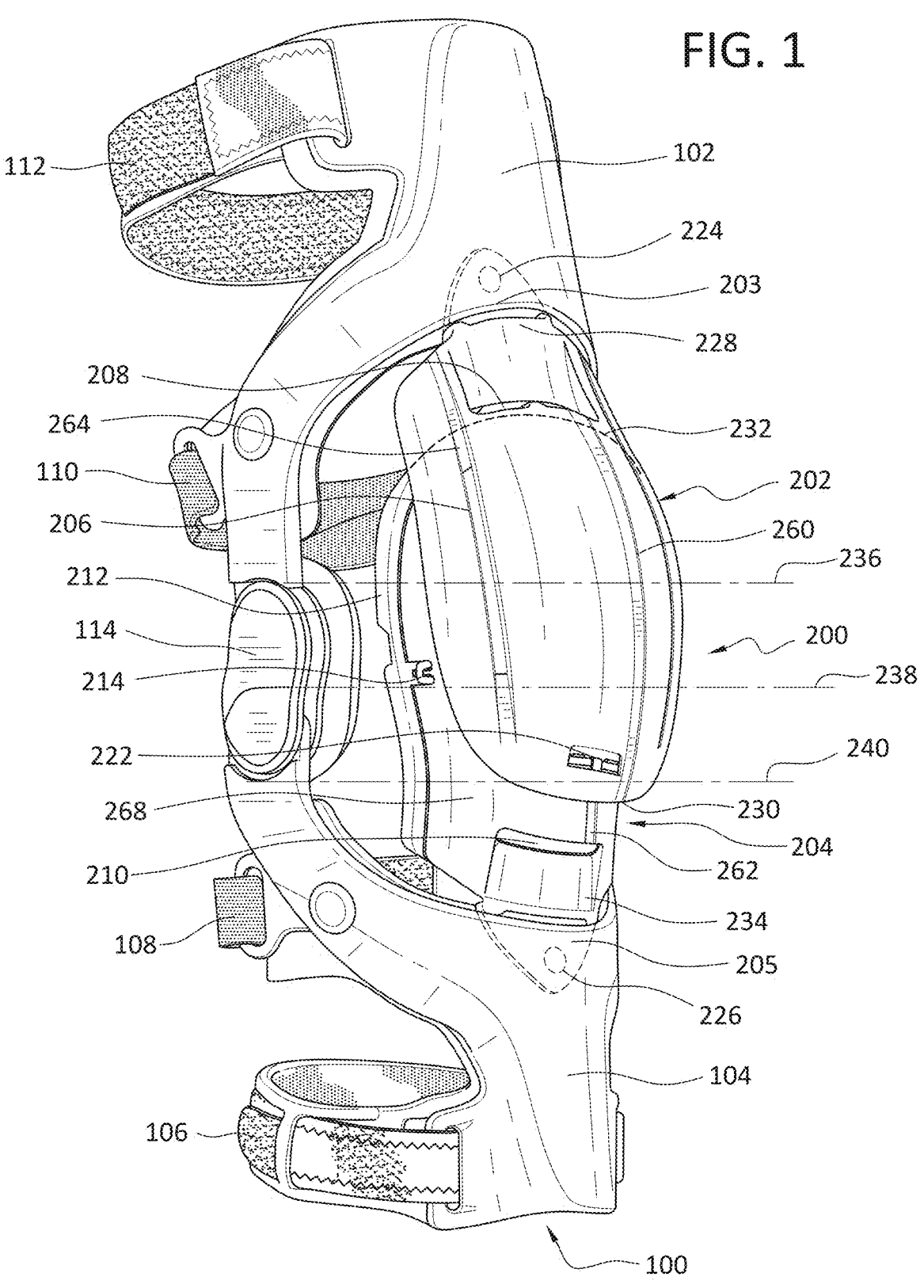
FIG. 1 is a perspective view of an impact guard in a knee brace according to the present disclosure.
Figure 2:
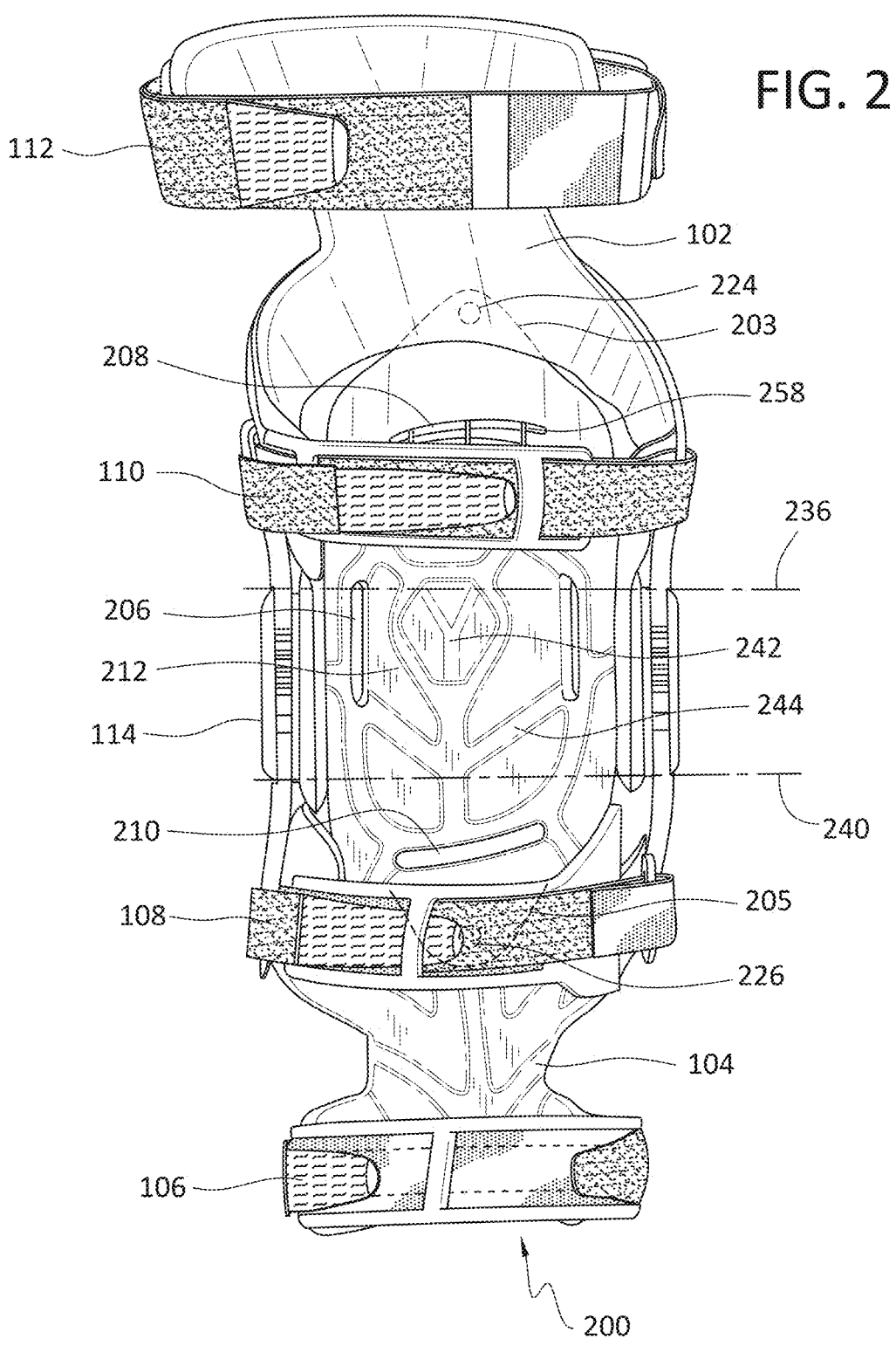
FIG. 2 is a plan view showing the rear of an impact guard and brace according to the present disclosure.

A better understanding of different embodiments of the disclosure may be had from the following description read with the accompanying drawings in which like reference characters refer to like elements.

While the disclosure is susceptible to various modifications and alternative constructions, certain illustrative embodiments are in the drawings and are described below. However, it should be understood that there is no intention to limit the disclosure to the embodiments disclosed; on the contrary, the intent is to cover all modifications, alternative constructions, combinations, and equivalents falling within the spirit and scope of the disclosure.

It will be understood that, unless a term is defined to possess a described meaning, there is no intent to limit the meaning of such term, either expressly or indirectly, beyond its plain or ordinary meaning.

B. Various Embodiments of an Impact guard for Use With a Knee Brace

The impact guard 200 advantageously is configured to be more straightforward in construction than existing patella guards for use with a knee brace. The impact guard may be employed with knee braces, and is advantageously simpler in construction and operation than the prior art impact guards, while providing the ability for the impact guard to accommodate movement of the knee.

The impact guard 200 may be secured to existing orthopedic devices. For this application, the exemplary orthopedic device or knee brace 100 to which the impact guard 200 is attached along an anterior side of the knee brace, is the knee brace described in U.S. Pat. App. Publ. No. 20200306070 A1, published on Oct. 10, 2020. The knee brace 100 consists of an upper frame 102 and a lower frame 104 connected by a hinge 114. The upper frame 102 is secured to the leg via an upper strap 112 and a lower strap 110. Likewise, the lower frame 104 is secured to the leg via an upper strap 108 and a lower strap 106.

The impact guard 200 is secured to the knee brace 100 at anchor points 203, 205. The anchor points 203, 205 are configured as openings 224, 226 for receiving a screw, nail, or similar attachment method. The first shell 202 is arranged with the anchor point 203 at the proximal or first end 228, and is preferably rigid. The second shell, 204, is arranged with the anchor point 205 on the distal or second end 234, and is preferably rigid.

The first and second shells may be arranged so they are assymetrical, as shown in the drawings, and include a liner or padding that is likewise assymetrical, for example the second shell may include the liner as the liner is arranged in contact with the user's knee as the hinge of the knee brace articulates. The second shell provides impact attenuation directly to the knee. The first shell provides secondary impact protection when a user is positioned deeper into flexion, and has more of the lower thigh exposed (such as a common area for handlebar strikes when a motocross rider falls over in a turn). The liner may be assymetrical since a knee is assymetrical, as well as the shells being assymetrical due to the shape of a knee and the need for articulating relative to one another (i.e., the first shell having a first central axis (A-A) articulating obliquely relative to a central second axis (B-B) of the second shell).

When connected to the brace 100, the first shell 202 is positioned in front of the second shell 204. At full leg extension, the center of the first shell 202 is positioned at the same height as the proximal end of the hinge 238. The distal end of the first shell 230 aligns with the distal end of the hinge 240. At full extension, the proximal end 232 of the second shell 204 reaches the top vent 208 of the first shell 202. The top vent 208 of the first shell 202 may be arranged with posts or ribs 258 extending from the vent down the inside of the first shell 202 to prevent the second shell 204 from blocking airflow.

The second shell 204 is attached to the lower frame 104 at an anchor point 205 and may provide the primary impact protection and be configured for placement over the knee's patella. The second shell 204 is preferably centered about the hinge 114, with the central line of the hinge 238 aligning with the center of the second shell 204 as observed by the position of the mounting posts 214, 22. The first shell 202 and the second shell 204 are secured by at least one replaceable elastic cord 216, which may be tethered to the shell via a security latch 220, and mounting posts 214.

The inclusion of an elastic portion in one or more of the straps of the orthopedic frame (112, 110, 108, 106) can maintain the central structure of the impact guard over the knee while accommodating movement of the knee as the user engages in twisting, pivoting, jumping, and similar movements as are common when engaging in motocross, skiing, or similar sports. Elastic portions of the straps are preferably concealed to avoid catching on objects unassociated with the knee brace 100. The impact guard 200 is arranged for maintaining continuous protection over the knee of the wearer regardless of flexion or extension of the knee. The first and second shells 202, 204 maintain a continuous relationship regardless of knee flexion. There are preferably no exposed gaps between the first and second shells 202, 204 regardless of knee flexion and extension.

Figure 3:
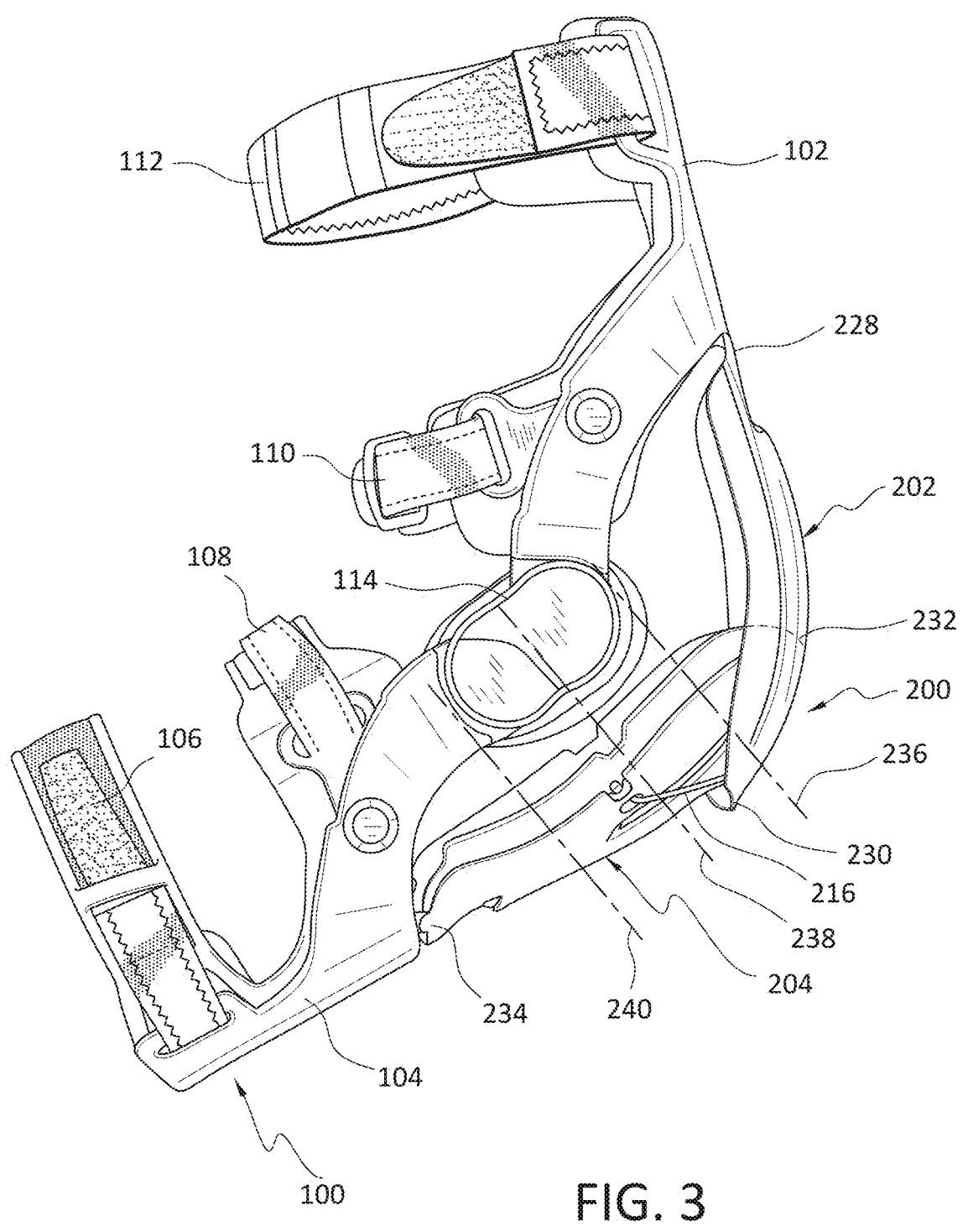
FIG. 3 is an elevational view of an impact guard and brace according to the present disclosure.
Figure 4:
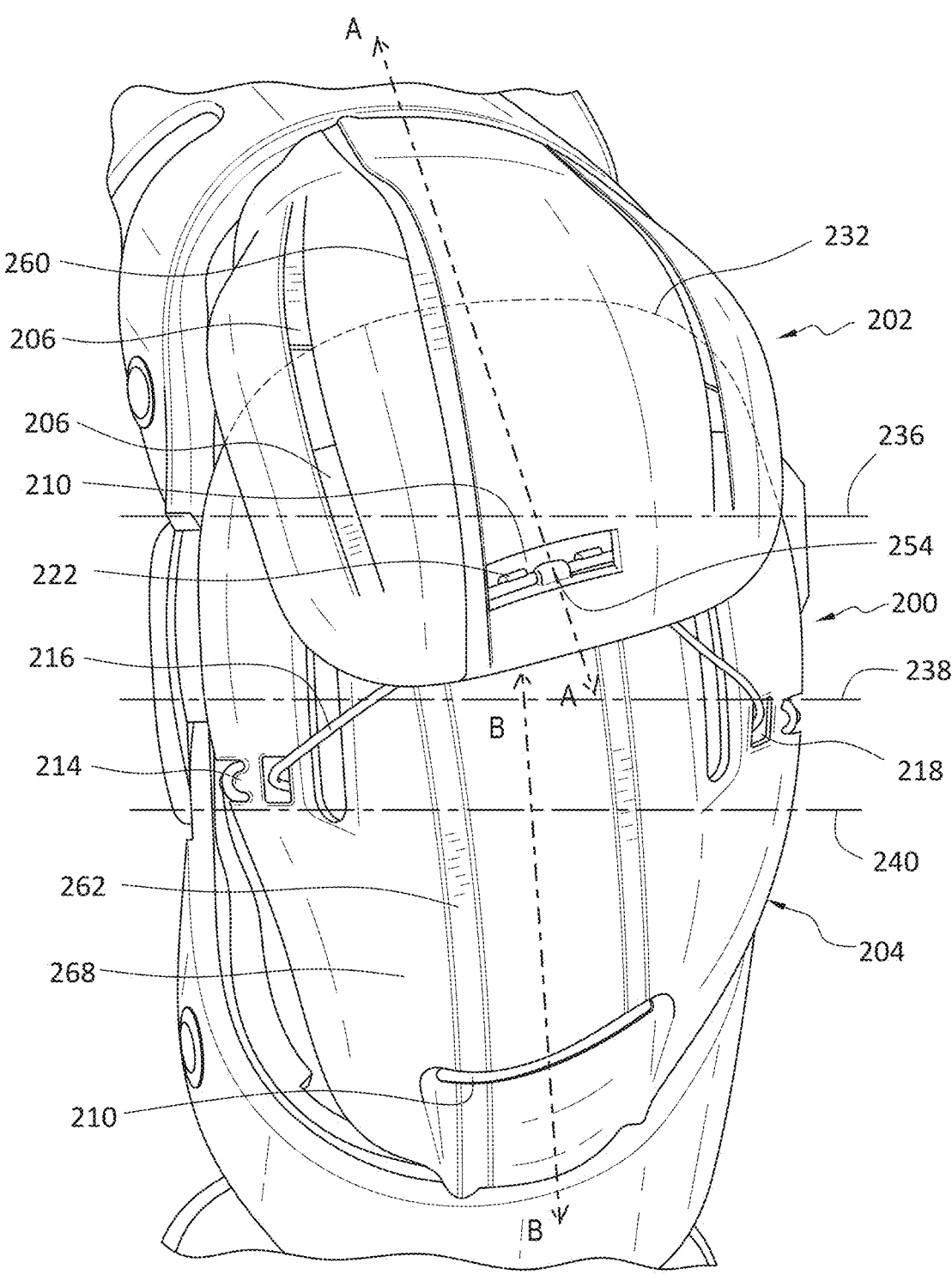
FIG. 4 is a plan view showing the front of the impact guard and brace in a bent position according to the present disclosure.

FIGS. 3 and 4 illustrate how the first shell 202 may move about the second shell 204 as the user bends the knee. The first shell 202 overlapping and the second shell 204 cover the knee while bending and are secured with the replaceable elastic cord 216. The elastic cord 216 may be threaded through the second shell 204 and EVA liner 212 via a hole 218 on either side of the second shell 204, preferably between the first and second ends. The elastic cord 216 may be secured to the mounting posts 214 of the second shell 204, preferably located at the second end of the first shell 202.

The mounting post 214 is arranged with a security latch 220 at the end to ensure the elastic cord 216 does not slip off during use. The mounting posts 222 in the first shell 202 are arranged at the vent 210. The elastic cords 216 are attached to the first shell's mounting posts 222 from the back, connecting the back of the first shell 202 to the front of the second shell 204. This arrangement allows the first shell 202 to track closely to the second shell 204 throughout use.

When the knee is bent, the second shell 204 remains in the same relative position as the hinge 114. The first shell 202 slides over the top of the second shell 204 while maintaining coverage. The distal or second end 230 of the first shell 202 does not retract further than the proximal line of the hinge 236. The second shell 204 and the first shell 202 overlap the patella of the user regardless of flexion and extension. In the bent position, the elastic cord 216 is in tension. The elastic cord 216 extends or loops around the mounting post 214 of the second shell and if fed through the opening 218 of the second shell 204 from the rear. The elastic cord 216 may be pulled in front of the first shell 202 and secured around the mounting post 222 of the first shell 202 from the back. The mounting posts 222 in the first shell 202 are found in the bottom vent 210.

The first shell 202 and the second shell 204 are arranged asymmetrically, curving towards the inside of the knee, and may be configured to fit either the right or the left knee. The second shell 204 may be arranged with a bottom vent 210 and two side vents 206. The second shell 204 may be arranged without a top vent as the area is always covered by the first shell 202 regardless of flexion or extension of the knee. Below the mounting post 214, the second shell define an indent 268 to follow the natural line of the leg. The second shell 204 may be arranged with a vertical ridge 262 extending from the proximal or first end 232 of the second shell 204 to the distal end of the second shell 234. The vertical ridge 262 curves slightly towards the inside of the knee to connect the tilted central masts of the upper and lower frames 102, 104.

Figures 5, 6:
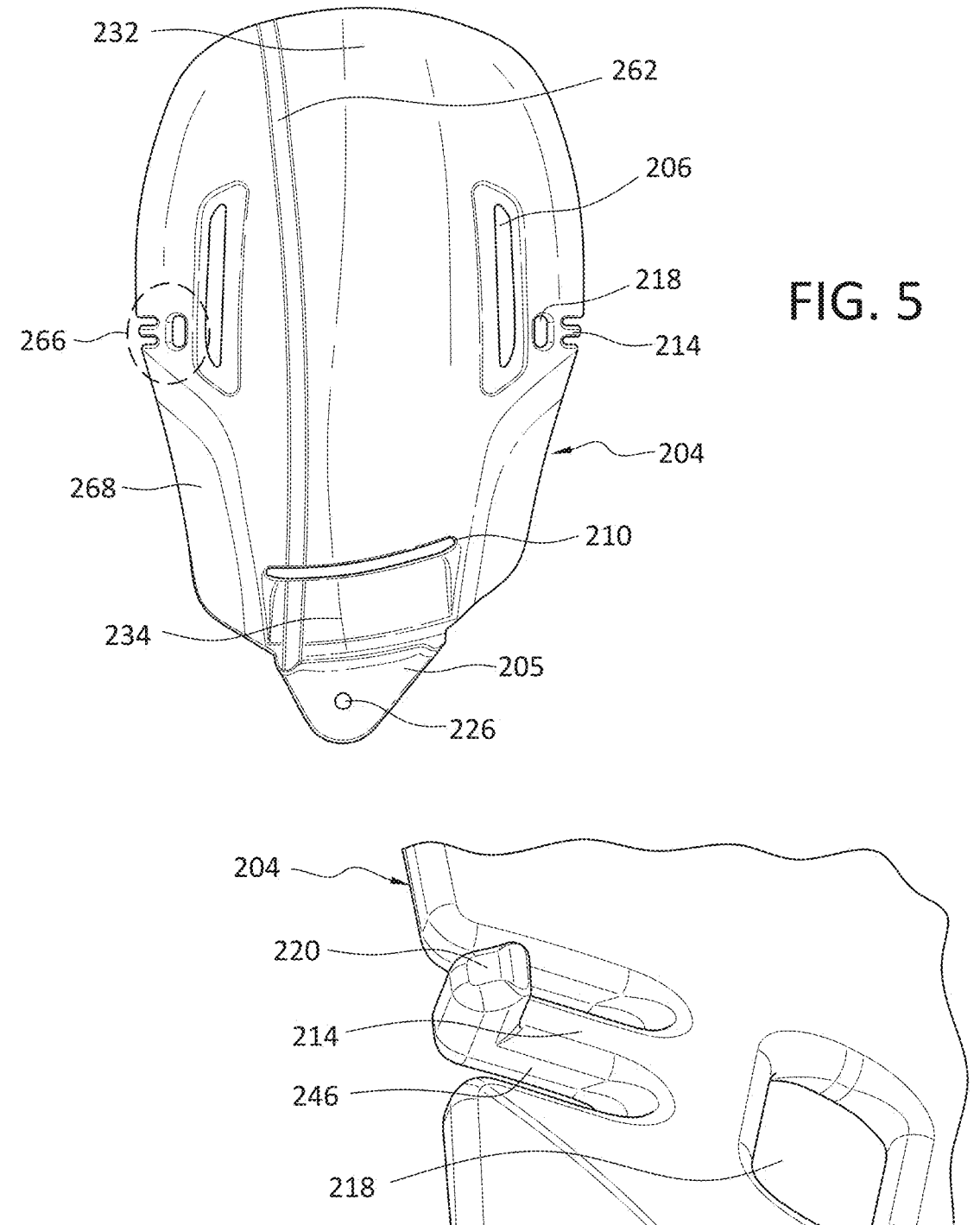
FIG. 5 is a plan view showing the front of the second shell of the impact guard according to the present disclosure.
FIG. 6 is a sectional view showing the second shell of the impact guard according to the present disclosure.

FIGS. 5 and 6 exemplify the mounting means 266 along the side of the second shell 204, as can be specifically seen in FIG. 6. A security latch 220 may be arranged to protrude from the end of the mounting post 214. The mounting post 214 is located between two notches 246, where the elastic cord 216 can be threaded through. The elastic cord 216 loops around the mounting post 214 and is threaded through the rear end of the opening 218. The security latch 220 can be located at the end of the mounting post 214 so that the elastic cord 216 does not slide off. The security latch 220 is tall enough to secure the elastic cord 216 when relaxed but short enough not to catch on outside material.

Figure 7:
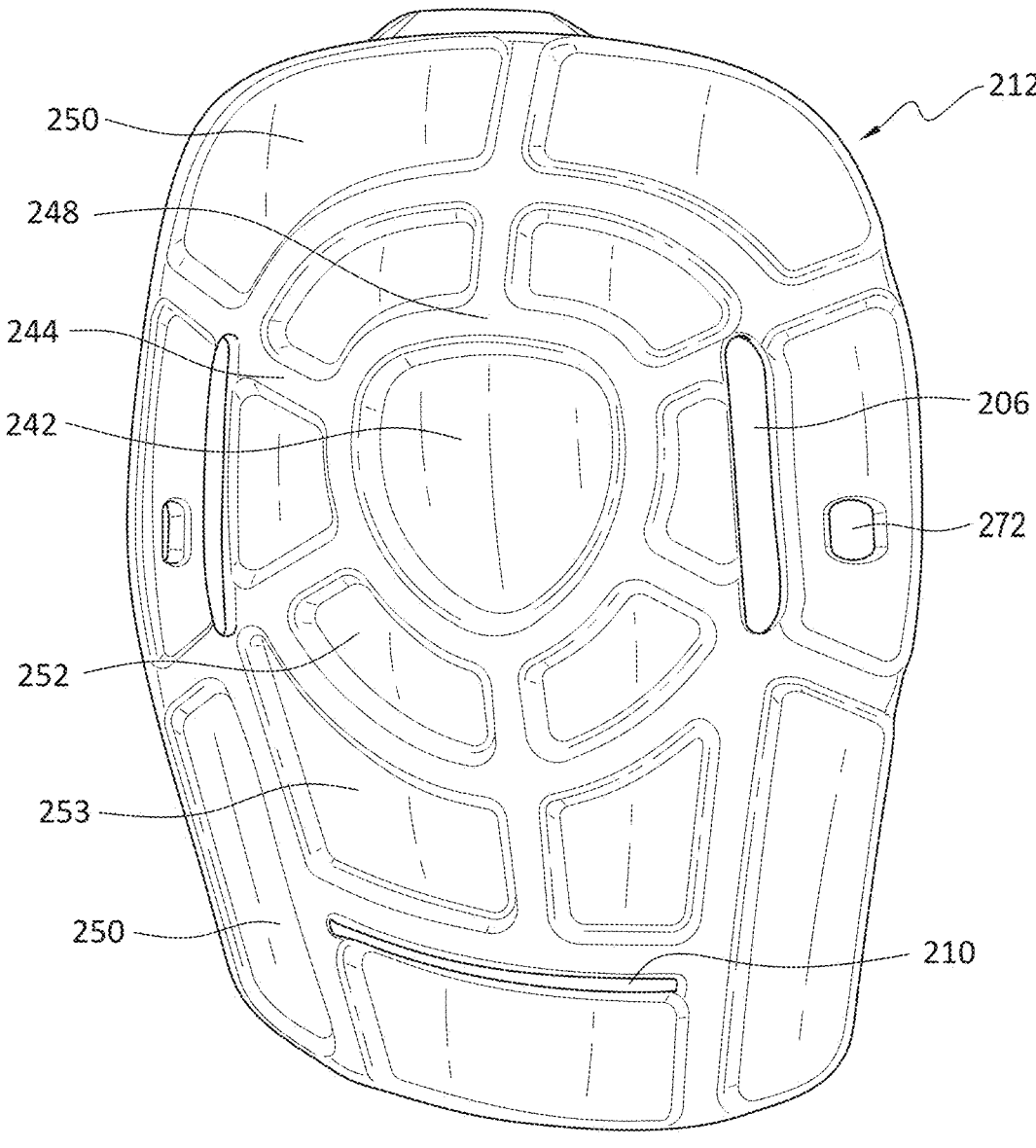
FIG. 7 is a plan view of the EVA liner of the second shell of the impact guard according to the present disclosure.
Figure 8:
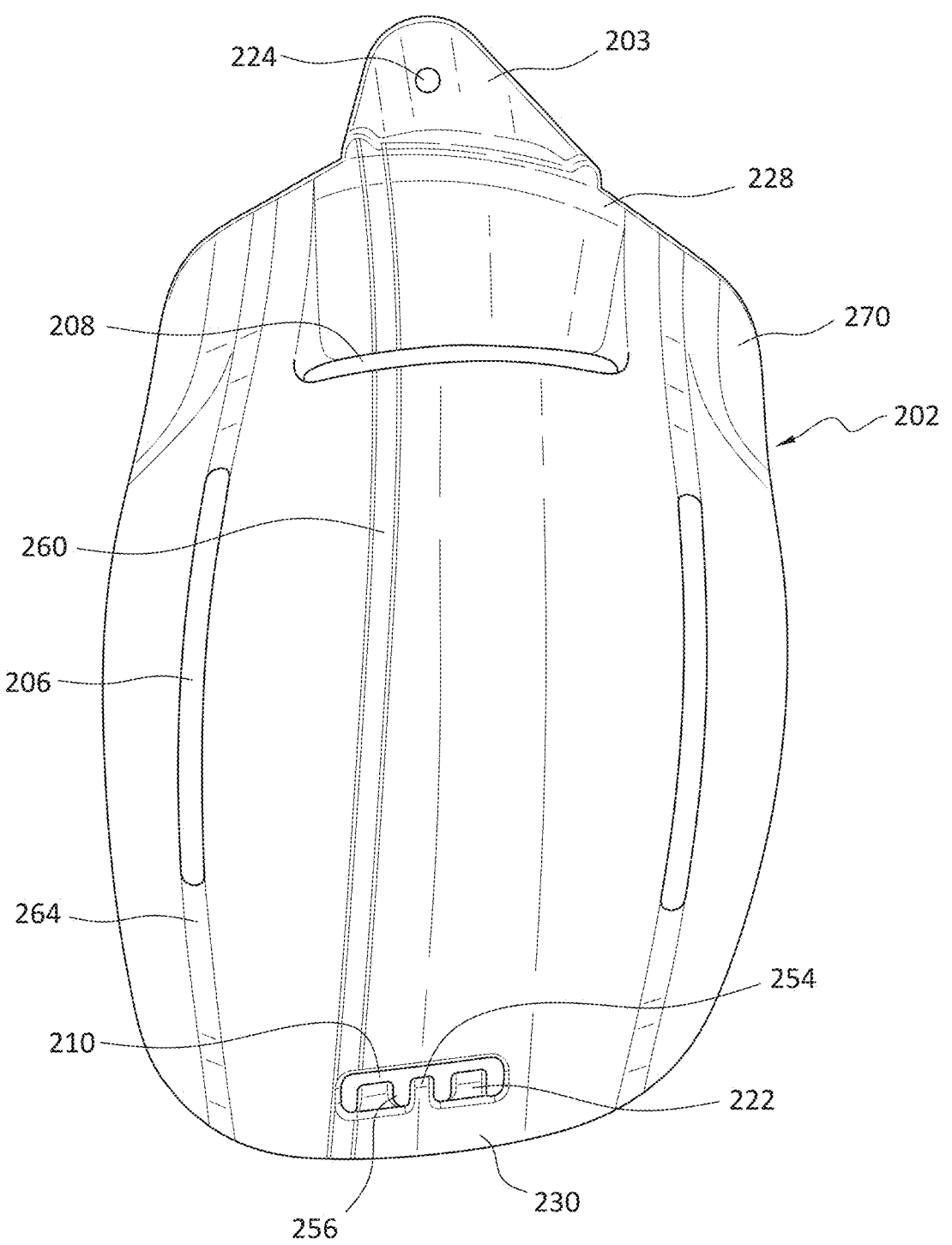
FIG. 8 is a plan view of the first shell of the impact guard according to the present disclosure.
Figure 9:
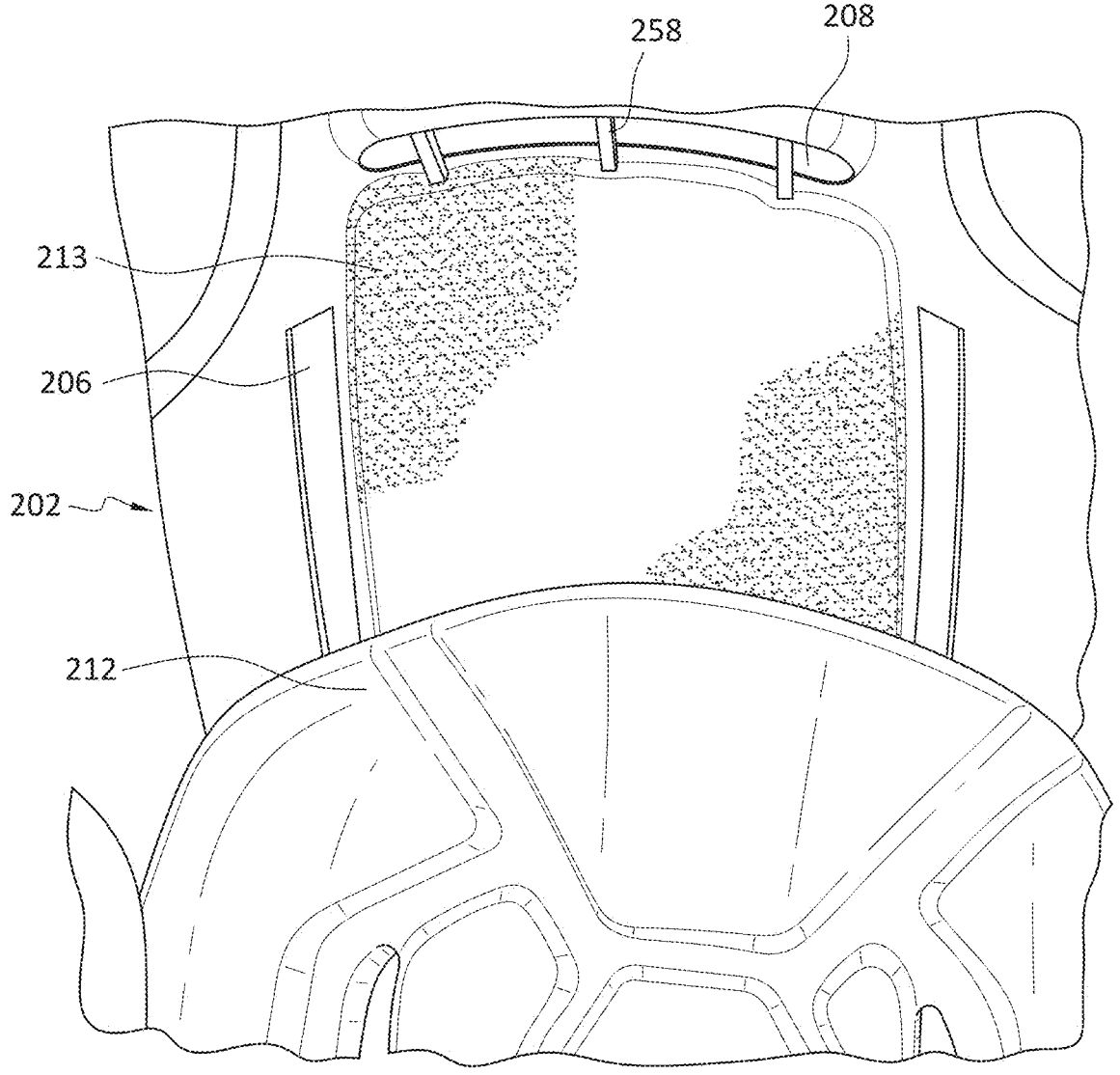
FIG. 9 is a plan view showing the rear of the impact guard in the bend position according to the present disclosure.

FIG. 7 through FIG. 9 illustrates that the second shell, 204 is lined with an EVA liner 212. The liner 212 may be attached to the second shell 204 by glue, overmolding, snaps, or any other method determined by one skilled in the art. The EVA liner 212 may be arranged to extend past the side edges of the second shell 204 for added protection. The center portion pad 242 of the EVA liner 212 is preferably arranged to be positioned directly over the patella of the user and align with the proximal line of the hinge 236.

The EVA liner 212 is configured in a pattern for impact attenuation while allowing airflow via molded-in cooling channel or channels 244. The pattern of the EVA liner 212 may be symmetric or nearly symmetric about a vertical central line 248. The center pad portion 242 may be shaped like the patella bone. The center pad portion 242 may be surrounded by a cooling channel 244, followed by a ring of pad segments 252. Openings 272 may be defined by the EVA liner 212 through the at least one elastic cord passes to engage the mounting posts 214, 222.

A preferred yet non-limitative embodiment includes the ring of pad segments 252 with a plurality of pads. At least one lower pad 253 may be arranged below the ring of pad segments 252. The at least one lower pad 253 may be included to add support below the knee. The outside border of the EVA liner 212 may be lined with side padding 250, which contours to the leg. The general shape of the EVA liner 212 may be arranged to fit into the second shell 204 and provide optimized protection and support for the patella. Various embodiments and configurations may be adopted by one skilled in the art.

The first shell 202 provides secondary impact protection and is preferably disposed above the patella, over the adjacent portion of the femur and quadriceps muscles during use. The first shell 202 has a bottom vent 210, two side vents 206 and a top vent 208. The side vents 206 of both the first shell 202 and the second shell 204 align when the user's knee is straight. The side vents 206 of the first shell 202 may be longer than the side vents of the second shell 204 to accommodate more air flow angles when the shells are maximally overlapped when the user's knee is straight.

The first shell 202 may be arranged with a vertical ridge 260 like the ridge 262 in the second shell 204. The ridge 260 of the first shell 202 and the ridge 262 of the second shell 204 may be arranged to align to verify correct placement. The first shell 202 may be arranged with indentations 270 on the proximal or first end 228 of the first shell 202. The indentations 270 may curve around the leg for increased protection. The side vents 206 on the first shell 202 may be arranged with ducts 264 on the top and bottom of the vents to aid in airflow.

The first shell 202 is arranged with a bottom vent 210, which may include mounting posts 222 to which the elastic cords 216 may attach. The elastic cord 216 may be threaded through the opening 256 on either side of the mounting post 222. The bottom vent 210 may include a central peg 254 to keep the elastic cords 216 separated. The mounting posts 222 may be curved outward away from the knee of the user, and the central peg 254 may be curved inwards towards the knee to secure the elastic cord 216.

The first shell 202 is arranged with the additional top vent 208 so that when the knee is bent, there is airflow access. The position of these vents allows the impact guard to retain the integrity needed for protection while increasing airflow. The vents are positions such that the patella of the user is wholly covered regardless of the knee position. The increased airflow protects the user from overheating the area while wearing the brace and increased comfort. The top vent 208 may be arranged with posts or ribs 258 for additional stability and may be used to prevent the second shell 204 from blocking the top vent 208.

The first shell 202 may be lined with EVA or Fabric die-cut lining 213. This lining is for secondary impact protection when a user is positioned deeper into flexion and has a more significant amount of the lower thigh exposed. The EVA/fabric liner 213 of the first shell 202 aids in noise reduction and adds the perception of additional comfort due to a softer fabric being used. The EVA or fabric lining 213 on the first shell 202 is positioned in the central portion of the shell between the side vents 206, below the top vent 208, and above the bottom vent 210.

Figure 10:
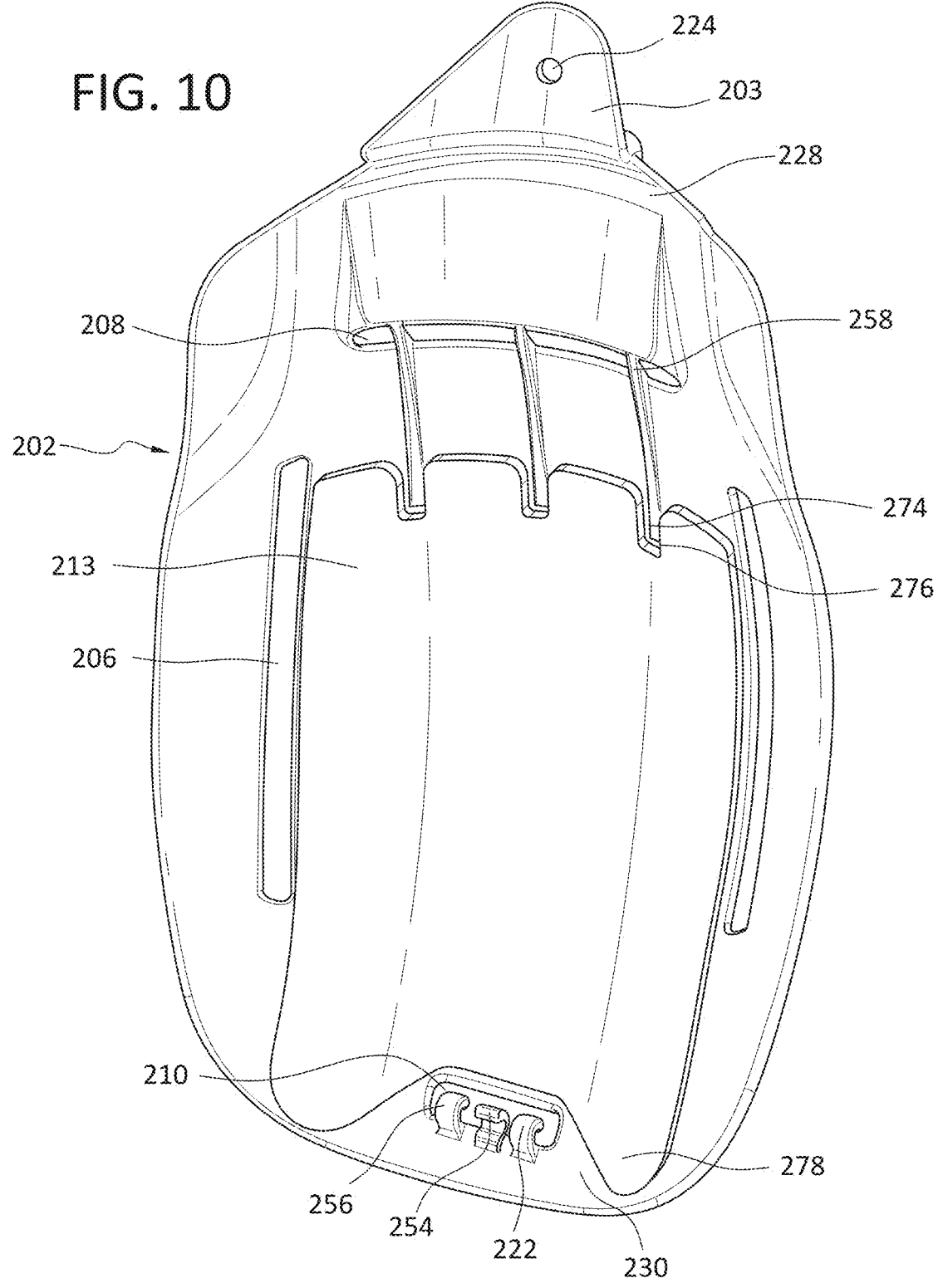
FIG. 10 is a plan view of the first shell and liner of the impact guard according to the present disclosure.

FIG. 10 further illustrates the possible position and shape of the EVA or Fabric die-cut lining 213 of the first shell 202. The lining 213 may extend the space between the side vents 206 and may have a length reaching from the distal or second end 230 of the first shell 202 to approximately the height of the top of the side vents 206. The liner 213 may extend past the bottom vent 210 on either side with rounded points 278, reaching the distal or second end 230 of the first shell 202. The proximal end of the liner 276 may have up to four extending portions, with up to three cut out segments 274 created to fit the posts or ribs 258 of the top vent of the first shell. The liner 213 may be attached to the first shell 202, for example, with an adhesive.

The first shell 202 and the second shell 204 may be thickest in the middle and thinner along the edge, providing stability and protection to the patella, while maintaining flexibility for the user.

While the orthopedic device has been described in a knee brace, it will be understood that the principles described may be extended to other types of orthopedic devices, braces or leg coverings.

Although this disclosure describes certain exemplary embodiments and examples of a patella shell or impact guard, it nevertheless will be understood by those skilled in the art that the present disclosure extends beyond the specifically disclosed embodiments to other alternative embodiments and/or users of the disclosure and obvious modifications and equivalents thereof. It is intended that the scope of the present disclosure should not be limited by the particular disclosed embodiments described above, and may be extended to other devices and supports, and other applications that may employ the features described herein.

The invention claimed is:

1. An impact guard for mounting to a knee brace, the impact guard comprising:
   a first shell having first and second ends;
   a second shell having first and second ends;
   at least one elastic cord connecting the first shell to the second shell;
   wherein the first and second shells are configured to cover at least a portion of a user's knee, the second shell being maintained stationary relative to a hinge of the knee brace as the first shell is configured to articulate relative to the second shell,
   wherein the at least one elastic cord extends along a front surface of the second shell and a rear surface of the first shell, such that the at least one elastic cord is attached to the first shell from the rear surface of the first shell.

2. The impact guard of claim 1, wherein a first portion of the at least one elastic cord is secured between opposed first and second sides of the second shell that extend generally perpendicular to the first and second ends of the second shell, and a second portion of the at least one elastic cord is secured to the second end of the first shell.

3. The impact guard of claim 2, wherein the first shell defines at least one mounting post proximate the second end and arranged for receiving the second portion of the at least one elastic cord.

4. The impact guard of claim 3, wherein the first shell defines a bottom vent, the first shell forms a central peg spaced apart from the at least one mounting post, the at least one mounting post including first and second mounting posts on opposed sides of the central peg.

5. The impact guard of claim 4, wherein the central peg is curved inwardly towards an inside concavity defined by the rear surface of the first shell, and the first and second mounting posts being curved outwardly relative to the central peg.

6. The impact guard of claim 1, wherein the second shell defines first and second posts on first and second sides about which the at least one elastic cord extends and is retained.

7. The impact guard of claim 6, wherein each of the first and second posts includes a latch retaining the at least one elastic cord from sliding off from the first and second posts.

8. The impact guard of claim 1, wherein the second end of the first shell is positionable over at least the first end of the second shell.

9. The impact guard of claim 1, wherein the second shell and the first shell are arranged asymmetrically relative to one another, as the first shell slides obliquely relative to a central axis of the second shell.

10. The impact guard of claim 1, wherein the second shell and the first shell are each arranged with a vertical ridge arranged to align with one another.

11. The impact guard of claim 1, wherein the second shell and the first shell are arranged with anchor points, the anchor points each define a hole configured to receive a fastener for securing to the knee brace.

12. The impact guard of claim 1, wherein the first shell defines a top vent forming posts or ribs arranged to prevent the first end of the second shell from blocking the top vent.

13. The impact guard of claim 1, further comprising an EVA liner located along an inside concavity of a rear of the second shell,
   wherein a center pad portion of the EVA liner is separated from a ring of pad segments by a cooling channel.

14. The impact guard of claim 1, wherein the first shell is configured to be positioned in front or over of the second shell, such that at a full leg extension, a center of the first shell is positioned at a same height as a proximal end of the hinge of the knee brace, the second end of the first shell is arranged to align with a distal end of the hinge,
   wherein at the full leg extension, the first end of the second shell reaches a top vent of the first shell.

* * * * *